United States Patent
Grammenos et al.

(10) Patent No.: US 6,372,766 B1
(45) Date of Patent: Apr. 16, 2002

(54) SUBSTITUTED 2-(2'-PYRIDYLOXY) PHENYLACETAMIDES, AS FUNGICIDES AND PESTICIDES

(75) Inventors: Wassilios Grammenos, Ludwigshafen; Klaus Oberdorf, Heidelberg; Hubert Sauter, Mannheim; Andreas Gypser, Mannheim; Herbert Bayer, Mannheim; Markus Gewehr, Kastellaun; Thomas Grote, Schifferstadt; Bernd Müller, Frankenthal; Arne Ptock, Ludwigshafen; Franz Röhl, Schifferstadt; Gerhard Hamprecht, Weinheim; Norbert Götz, Worms; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,806

(22) PCT Filed: Oct. 21, 1998

(86) PCT No.: PCT/EP98/06683

§ 371 Date: Apr. 20, 2000

§ 102(e) Date: Apr. 20, 2000

(87) PCT Pub. No.: WO99/21833

PCT Pub. Date: May 6, 1999

(30) Foreign Application Priority Data

Oct. 29, 1997 (DE) .......................... 197 47 788

(51) Int. Cl.[7] ..................... A01N 43/40; C07D 213/64; C07D 213/69; C07D 213/78
(52) U.S. Cl. ................. 514/346; 514/351; 546/296; 546/300; 546/302
(58) Field of Search ................ 546/296, 302, 546/300; 514/351, 346

(56) References Cited

U.S. PATENT DOCUMENTS 5,770,614 A * 6/1998 Murabayashi et al. ...... 514/348

FOREIGN PATENT DOCUMENTS

| EP | 398 692 | 11/1990 |
|----|---------|---------|
| EP | 596 692 | 5/1994 |
| EP | 617 001 | 9/1994 |
| EP | 629 609 | 12/1994 |
| EP | 760 363 | 3/1997 |
| WO | 97/30032 | 8/1997 |

* cited by examiner

Primary Examiner—Alan L. Rotman
(74) Attorney, Agent, or Firm—Keil & Weinkauf

(57) ABSTRACT

Substituted 2-(2'-pyridyloxy)phenylacetamides I,

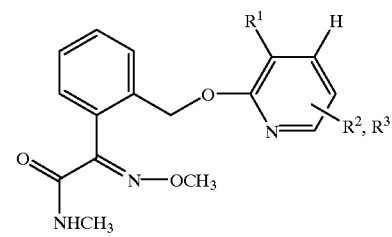

(I)

where $R^1$ is fluorine, chlorine, $CH_3$ or halomethyl;

$R^2$ is fluorine, bromine, alkyl or halomethyl;

$R^3$ is hydrogen or one of the radicals mentioned under $R^2$; and $R^2$ is 6-chloro if $R^3$ is hydrogen, $R^3$ is 5-chloro if $R^2$ is fluorine and the compound in which $R^1$, $R^2$ and $R^3$ are each chlorine with the proviso that $R^1$ may not be chlorine if $R^2$ is 5-trifluoromethyl and $R^3$ is hydrogen, and processes for their preparation and their use for controlling harmful fungi and animal pests are described.

11 Claims, No Drawings

SUBSTITUTED 2-(2'-PYRIDYLOXY) PHENYLACETAMIDES, AS FUNGICIDES AND PESTICIDES

This application is a 371 of PCT/EP98/06683 Oct. 21, 1998.

The present invention relates to substituted 2-(2'-pyridyloxy)phenylacetamides of the formula I,

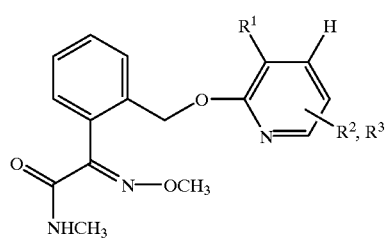

where
R$^1$ is fluorine, chlorine, CH$_3$ or halomethyl;
R$^2$ is fluorine, bromine, C$_1$–C$_4$-alkyl or halomethyl;
R$^3$ is hydrogen or one of the radicals mentioned under R$^2$;
or
R$^2$ is 6-chloro if R$^3$ is hydrogen,
R$^3$ is 5-chloro if R$^2$ is fluorine,
and the compound in which R$^1$, R$^2$ and R$^3$ are each chlorine;
with the proviso that R$^1$ may not be chlorine if R$^2$ is 5-trifluoromethyl and R$^3$ is hydrogen.

Furthermore, the invention relates to processes for preparing the compounds I, and to compositions and to the use of the compounds I for controlling harmful fungi and animal pests.

α-Phenyl-α-alkoximinoacetamides having heteroaryloxy groups in ortho position are disclosed in EP-A 398 692, EP-A 629 609 and EP-A 760 363. The compounds described in the abovementioned publications are suitable for use as crop protection agents in harmful fungi, and some of them for use as bactericides.

However, their activity is not always entirely satisfactory. It is an object of the present invention to provide compounds having improved activity.

We have found that this object is achieved by the phenylacetic acid derivatives of the formula I. Furthermore, we have found processes for preparing the compounds I, and the use of the compounds I and of compositions comprising them for controlling harmful fungi and animal pests. Preference is given to the fungicidal activity.

The compounds of the formula I differ from the compounds known from the abovementioned publications in the substitution of the 2-pyridinyloxy group which has to be substituted in position 3 by the radical R$^1$ which has a particular structure, and unsubstituted in position 4. The compounds of the formula I have improved activity against harmful fungi and animal pests in comparison with the prior art compounds.

The compounds of the formula I can be obtained by methods similar to those described in EP-A 760 363.

In particular, the compounds of the formula Ia are obtained by the following synthetic route:

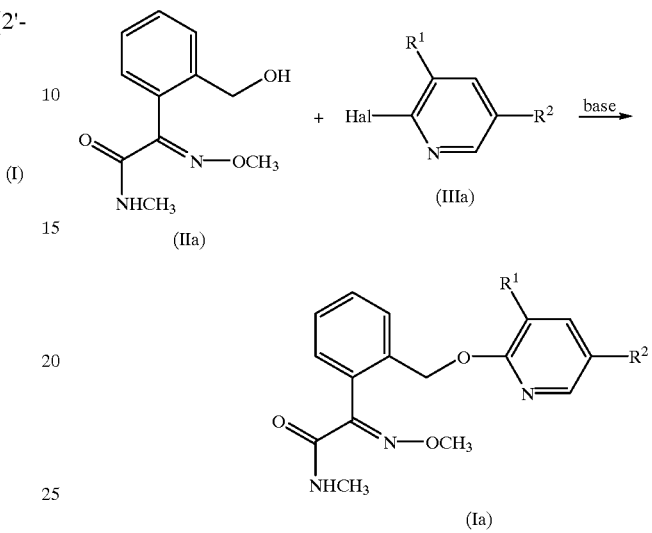

The condensation of the benzyl alcohol of the formula IIa with 2-halopyridines of the formula IIIa in which [Hal] is halogen, for example chlorine or bromine, is carried out under conditions known per se [cf. EP-A 760 363; EP-A 398 692].

2-Halopyridines of the formula IIIa are either commercially available, or they can be prepared by methods known from the literature [cf. U.S. Pat. No. 4,279,913; U.S. Pat. No. 4,491,468; JP-A 58/206 563; J. Org. Chem. (1989), p. 1726ff.].

2-Halopyridines of the formula IIIa are also obtainable from the 2-hydroxypyridines of the formula IIIb' by halogenation, for example using POCl$_3$. The halogenation is carried out under known conditions [cf. Houben-Weyl, Methoden der Organischen Chemie, Vol. 5/3, 4th Edition, p. 924ff., Thieme Verlag Stuttgart and New York (1962)].

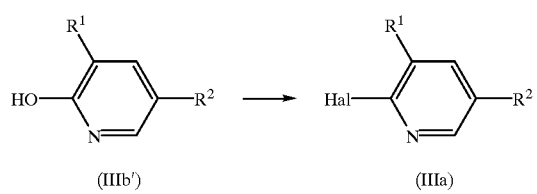

The benzyl alcohol of the formula hIa is also known from the literature and can be obtained under known conditions [cf. EP-A 398 692].

The compounds of the formula Ib are obtained in a particularly advantageous manner via the corresponding esters of the formula IV, by the following synethic route:

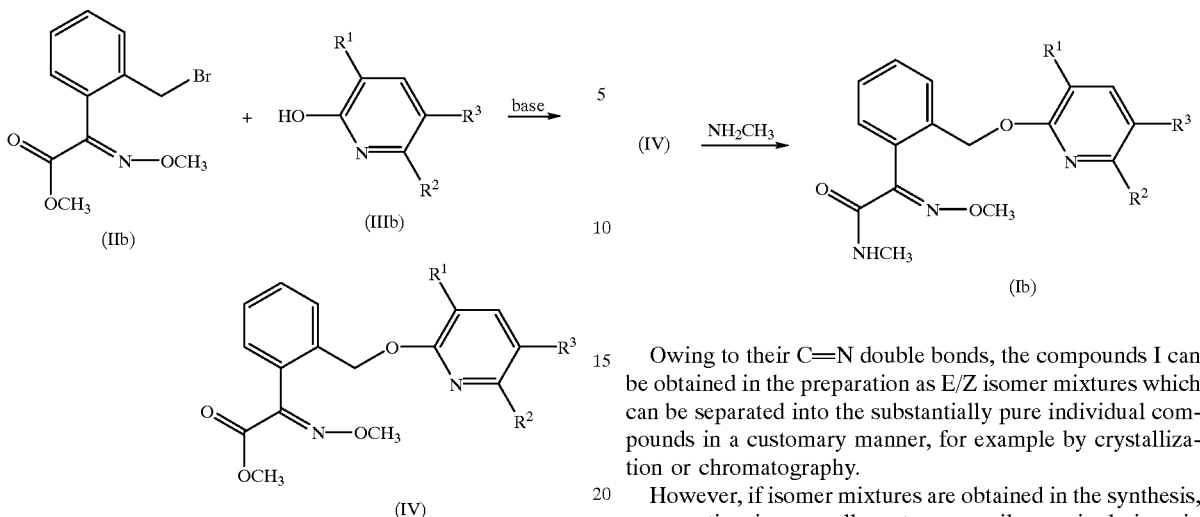

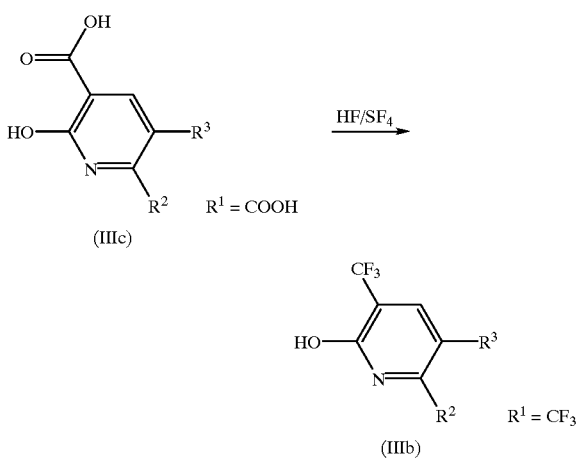

The condensation of the benzyl bromide of the formula IIb with 2-hydroxypyridines of the formula IIIb is carried out under conditions known per se [cf. DE-A 38 35 028].

The benzyl bromide of the formula IIb is also known from the literature and can be obtained under known conditions [cf. EP-A 420 091; DE-A 39 17 351].

2-Hydroxypyridines of the formula IIIb are either commercially available or they can be obtained by methods similar to those known from the literature. 2-Hydroxypyridines in which $R^1$, $R^2$ or $R^3$ are $CF_3$ are preferably obtained from the commerically available 2-hydroxypyridinecarboxylic acids IIIc by reaction with hydrogen fluoride and sulfur tetrafluoride [cf. DE-A 3 620 064].

Compounds IIIb in which $R^1$ is $CF_3$ are, for example, obtained from 2-hydroxypyridine-3-carboxylic acids of the formula IIIc by the following reaction:

2-Hydroxypyridinecarboxylic acids IIIc are also known from the literature [cf. EP-A 225 172; U.S. Pat. No. 4,960, 896; U.S. Pat. No. 5,034,531], or they can be prepared by methods similar to those in the literature quoted.

The amidation of the esters of the formula IV is preferably carried out under known conditions using methylamine [cf. EP-A 398 692].

Owing to their C=N double bonds, the compounds I can be obtained in the preparation as E/Z isomer mixtures which can be separated into the substantially pure individual compounds in a customary manner, for example by crystallization or chromatography.

However, if isomer mixtures are obtained in the synthesis, a separation is generally not necessarily required since in some cases the individual isomers can be converted into each other during preparation for use or upon use (for example under the influence of light, acids or bases). Corresponding conversions may also occur after the application, for example in the treatment of plants, in the treated plant or in the harmful fungi or animal pest to be controlled.

With regard to the C=N—OCH$_3$ double bond, preference is given to the E isomers of the compounds I with respect to their activity (configuration based on the OCH$_3$ group in relation to the CONHCH$_3$ group).

In the definitions of the symbols given in the above formulae, collective terms were used which generally represent the following substituents:

$C_1$–$C_4$-Alkyl: saturated, straight-chain or branched hydrocarbon radicals having 1 to 4 carbon atoms, such as methyl, ethyl, propyl, 1-methylethyl, butyl, 1-methylpropyl, 2-methylpropyl and 1,1-dimethylethyl;

Halomethyl: methyl groups in which some or all of the hydrogen atoms may be replaced by halogen atoms, for example chloromethyl, bromomethyl, dichloromethyl, trichloromethyl, fluoromethyl, difluoromethyl, trifluoromethyl, chlorofluoromethyl, dichlorofluoromethyl and chlorodifluoromethyl.

With regard to the intended use of the pyridineoxyamides [sic] of the formula I, particular preference is given to the following meanings of the substituents, in each case either alone or in combination:

Preference is given to compounds Ia in which $R^1$ is methyl.

Likewise, particular preference is given to compounds Ia in which $R^2$ is trifluoromethyl.

Additionally, particular preference is given to compounds Ia in which $R^1$ is fluorine or chlorine.

Especially preferred are also compounds Ia in which $R^1$ is trifluoromethyl.

Furthermore, particular preference is given to compounds Ia in which $R^1$ is $C_1$–$C_4$-alkyl.

Especially preferred are compounds Ia in which $R^2$ is fluorine or bromine.

Furthermore, particular preference is given to compounds Ib in which $R^1$ is trifluoromethyl.

Furthermore, particular preference is given to compounds Ib in which $R^1$ is fluorine or chlorine.

Likewise, particular preference is given to compounds Ib in which $R^2$ is trifluoromethyl.

Moreover, particular preference is given to compounds Ib in which $R^3$ is hydrogen.

Additionally, particular preference is given to compounds Ib in which $R^2$ is chlorine and $R^3$ is hydrogen.

Furthermore, particular preference is given to compounds I in which $R^1$ is fluorine, chlorine, $CH_3$ or $CF_3$; $R^2$ is fluorine, bromine, $C_1$–$C_4$-alkyl or $CF_3$; $R^3$ is hydrogen or one of the radicals mentioned under $R^2$.

Especially preferred are the 2-(2'-pyridyloxy) phenylacetamides of the formula Ia, in particular the compounds listed in Table A below:

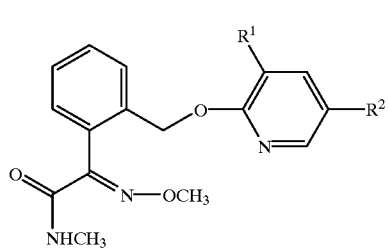

(Ia)

TABLE A

| No. | $R^1$ | $R^2$ |
|---|---|---|
| A-1 | methyl | trifluoromethyl |
| A-2 | fluoro | trifluoromethyl |
| A-3 | methyl | difluoromethyl |
| A-4 | fluoro | difluoromethyl |
| A-5 | chloro | difluoromethyl |
| A-6 | methyl | fluoro |
| A-7 | fluoro | fluoro |
| A-8 | chloro | fluoro |
| A-9 | methyl | bromo |
| A-10 | fluoro | bromo |
| A-11 | chloro | bromo |
| A-12 | trifluoromethyl | trifluoromethyl |
| A-13 | trifluoromethyl | fluoro |
| A-14 | trifluoromethyl | bromo |
| A-15 | trifluoromethyl | methyl |
| A-16 | trifluoromethyl | ethyl |
| A-17 | trifluoromethyl | n-propyl |
| A-18 | trifluoromethyl | isopropyl |
| A-19 | trifluoromethyl | n-butyl |
| A-20 | trifluoromethyl | isobutyl |
| A-21 | trifluoromethyl | tert-butyl |

Among the compounds Ib, particular preference is given to the compounds listed in Table B below:

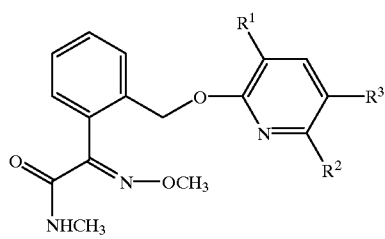

(Ib)

TABLE B

| No. | $R^1$ | $R^2$ | $R^3$ |
|---|---|---|---|
| B-1 | methyl | trifluoromethyl | H |
| B-2 | methyl | difluoromethyl | H |
| B-3 | methyl | fluoro | H |
| B-4 | methyl | bromo | H |
| B-5 | methyl | methyl | H |
| B-6 | methyl | ethyl | H |
| B-7 | methyl | n-propyl | H |
| B-8 | methyl | isopropyl | H |
| B-9 | methyl | n-butyl | H |
| B-10 | methyl | isobutyl | H |
| B-11 | methyl | tert-butyl | H |
| B-12 | fluoro | trifluoromethyl | H |
| B-13 | fluoro | difluoromethyl | H |
| B-14 | fluoro | fluoro | H |
| B-15 | fluoro | bromo | H |
| B-16 | fluoro | methyl | H |
| B-17 | fluoro | ethyl | H |
| B-18 | fluoro | n-propyl | H |
| B-19 | fluoro | isopropyl | H |
| B-20 | fluoro | n-butyl | H |
| B-21 | fluoro | isobutyl | H |
| B-22 | fluoro | tert-butyl | H |
| B-23 | chloro | trifluoromethyl | H |
| B-24 | chloro | difluoromethyl | H |
| B-25 | chloro | fluoro | H |
| B-26 | chloro | bromo | H |
| B-27 | chloro | methyl | H |
| B-28 | chloro | ethyl | H |
| B-29 | chloro | n-propyl | H |
| B-30 | chloro | isopropyl | H |
| B-31 | chloro | n-butyl | H |
| B-32 | chloro | isobutyl | H |
| B-33 | chloro | tert-butyl | H |

The compounds I are suitable as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
Fusarium and Verticillium species on various plants,
Helminthosporium species on cereals,
Mycosphaerella species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
Pseudoperonospora species on hops and cucumbers, Puccinia species on cereals,

*Pyricularia oryzae* on rice,

Rhizoctonia species on cotton, rice and lawns,

*Septoria nodorum* on wheat,

*Uncinula necator* on grapevines,

Ustilago species on cereals and sugar cane, and

Venturia species (*scab*) on apples and pears.

Moreover, the compounds I are suitable for controlling harmful fungi such as *Paecilomyces variotii* in the protection of materials (eg. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Eariag ingulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Eyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus* [sic] *sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina* [sic], *Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum*

*euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii*, termites (Isoptera), eg. *Calotermes flavicollis, Leucotermes flavipes, Reticulitermes lucifugus* and *Termes natalensis*, orthopterans (Orthoptera), eg. *Acheta domestica, Blatta orientalis, Blattella germanica, Forficula auricularia, Gryllotalpa gryllotalpa, Lōcusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae*, nematodes such as root knot nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; in any case, it should guarantee a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for scattering and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silica gel, silicas, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. parts by weight of a compound according to the invention are mixed intimately with 95 parts by weight of finely divided kaolin. This gives a dust which comprises 5% by weight of the active ingredient.

II. parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamde, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4- oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, methyl-E-methoxyimino-[α-(2-phenoxyphenyl)]-acetamide, methyl E-methoxyimino-[α-(2,5-dimethylphenoxy)-o-tolyl]acetamide, anilinopyrimidines such as N-(4, 6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxy-phenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4,4-dichlorophenyl)pentyl]-1H-1,2,4-triazole, 2,4-difluoro-α-(1H-1,2,4-triazolyl-l-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLE

With due modification of the starting compounds, the protocols shown in the synthesis examples below were used for obtaining further compounds I. The resulting compounds, together with physical data, are listed in the Table which follows.

Example 1

Preparation of α-anti-methoxyimino-N-methyl-2-(3-fluoro-5-trifluoromethyl-2-pyridyloxy)methylphenyl-acetamide (No. I-1)

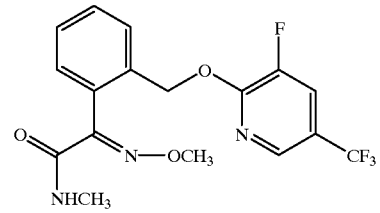

A suspension of 1.4 g of sodium hydride in 15 ml of dimethylformamide (DMF) was mixed with a solution of 11.1 g of (E) -2-[2-(hydroxymethyl) phenyl]-2-methoxyimino-N-methylacetamide in 120 ml of DMF. The reaction mixture was exposed to ultrasound for about 10 min and subsequently stirred at about 20 to 25° C. for 1 h. A solution of 9.2 g of 2,3-difluoro-5-trifluoromethyl-pyridine in 85 ml of DMF was added dropwise and the mixture was stirred at 22 to 25° C. for about 24 h. The reaction mixture was taken up in 1 l of dilute sodium chloride solution and extracted with methyl tert-butyl ether (MtBE). The combined organic phases were washed with water and dried. The solvent was distilled off under reduced pressure and the residue was subjected to silica gel chromatography (cyclohexane/MtBE=2:1), affording 6.9 g of the title compound as a pale powder of mp. 112–116° C.

IR (cm$^{-1}$): 3380, 1659, 1623, 1498, 1453, 1336, 1272, 1151, 1131, 1040.

Example 2

Preparation of 2-chloro-3-methyl-5-iodopyridine

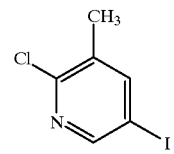

At −10° C., 21.3 g of chlorine gas were introduced into a suspension of 146 g of 10% strength by weight hydrochloric acid and 23.4 g of 2-amino-3-methyl-5-iodopyridine [J. Org. Chem. (1995), p. 5356]. At about −50° C., a solution of 48.3 g of sodium nitrite in 120 ml of water was subsequently added dropwise. After about 2 hours of stirring at 0° C., the mixture was diluted with 1 l of water and extracted with methyl tert-butyl ether (MtBE). The organic phases were washed with NaHCO$_3$ solution and water and then dried. Distillative removal of the solvent under reduced pressure and silica gel chromatography (cyclohexane/MtBE=1:10) gave 3.6 g of the product in the form of dark crystals.

$^1$H-NMR (CDCl$_3$, ppm): δ=8.4 (1H); 7.9 (1H); 2.3 (3H).

Example 3

Preparation of 2-chloro-3-methyl-5-trifluoromethylpyridine

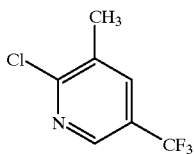

A solution of 84.7 g of the pyridine derivative from Example 2 in 1 l of N-methylpyrolidone was admixed with 136.3 g of sodium trifluoroacetate and 95.2 g of CuI and stirred at 160° C. for 2 h. After cooling, the mixture was taken up in about 3 l of water and extracted with ethyl acetate. The combined organic phases were washed with 2.5% strength by weight of aqueous ammonia solution and water, dried and subsequently freed from the solvent under reduced pressure. The remaining crude product gave, after rectification over a short column, 14.3 g of the title compound of bp. 70–75° C. (at 25 mbar) as a colorless oil.

$^1$H-NMR (CDCl$_3$, ppm): δ=8.6 (1H); 7.8 (1H); 2.4 (3H).

Example 4

Synthesis of α-anti-methoxyimino-N-methyl-2-(3-methyl-5-trifluoromethyl-2-pyridyloxy)methyl-phenylacetamide (No. I-2)

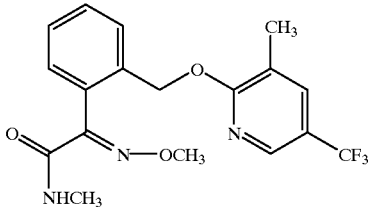

A solution of 23.8 g of (E)-2-[2-(hydroxymethyl)phenyl]-2-methoxyimino-N-methylacetamide in 200 ml of dimethylformamide (DMF) was mixed with a suspension of 2.82 g of sodium hydride in 25 ml of DMF. The reaction mixture was exposed to ultrasound for about 10 min and subsequently stirred at 20 to 25° C. for 1 h. A solution of 20.9 g of 2-chloro-3-methyl-5-trifluoromethylpyridine (from Example 3) in 150 ml of DMF was added dropwise, and the mixture was stirred for 3 hours at 45° C. and for a further 24 hours at 22–25° C. The reaction mixture was taken up in 3 l of dilute sodium chloride solution and extracted with methyl tert-butyl ether (MtBE). The combined organic phases were washed with water, dried and freed from the solvent under reduced pressure. Silica gel chromatography (cyclohexane/MtBE=1:1) of the residue gave 15.8 g of the title compound as a white powder of mp. 133–135° C.

IR (cm$^{-1}$): 1672, 1418, 1335, 1324, 1269, 1264, 1173, 1145, 1123, 1038.

TABLE I (Ia)

(Ib)

| No. | Formula | R$^1$ | R$^2$ | R$^3$ | Phys. data (mp. [° C.], IR [cm$^{-1}$]) |
|---|---|---|---|---|---|
| I-1 | Ia | F | CF$_3$ | — | 110–112 |
| I-2 | Ia | CH$_3$ | CF$_3$ | — | 125–130 |
| I-3 | Ib | CF$_3$ | Cl | H | 103–105 |
| I-4 | Ib | CH$_3$ | CH$_3$ | H | 116–118 |
| I-5 | Ib | Cl | Cl | Cl | 147–148 |
| I-6 | Ib | Cl | Cl | CF$_3$ | 139–141 |
| I-7 | Ib | Cl | F | CF$_3$ | 108–111 |
| I-8 | Ia | Cl | CHF$_2$ | — | 1669, 1605, 1474, 1352, 1069, 1036, 988 |

EXAMPLES OF THE ACTION AGAINST HARMFUL FUNGI

The fungicidal action of the compounds of the formula I was demonstrated by the following experiments:

The active compounds, separately or together, were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

The substances known from EP-A 398 692 (Table 7, No. 78; compound A) and from EP-A 760 363 (No. 9; compound B) served as comparative active compounds:

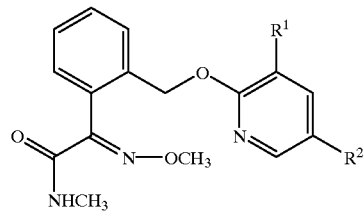

Use Example 1

Action Against *Plasmopara Viticola*

Leaves of potted vines of the variety "Müller-Thurgau" were sprayed to runoff point with an aqueous active compound preparation prepared from a stock solution of 10% of active compound, 63% of cyclohexanone and 27% of emulsifier. To be able to assess the long-term activity of the substances, the plants were kept in a greenhouse for 7 days after the spray coating had dried on. Only then were the leaves inoculated with an aqueous zoospore suspension of *Plasmopara viticola*. The vines were then first kept in a chamber saturated with water vapor at 24° C. for 48 hours, and subsequently in a greenhouse at 20–30° C. for 5 days. After this time, the plants were once more placed in a humid chamber for 16 hours to promote the eruption of sporangiophores. The extent of the fungal infection on the underside of the leaves was then determined visually.

In this test, the plants which had been treated with 4 ppm of the compounds I-1, I-2, I-3, I-5, I-6, I-7 and I-8 showed an infection of not more than 15%, while the plants that had been treated with 4 ppm of the comparative compounds A and B were infected to 60 and 50%, respectively, and untreated plants were infected to 75%.

Use Example 2

Long-term Action Against *Phytophthora Infestans* on Tomatoes

Potted tomato plants (c.v. "*Große Fleischtomate*") in the 4-leaf stage were sprayed to runoff point with an aqueous suspension made up of a stock solution of 10% of active compound, 63% of cyclohexanone and 27% of emulsifier. To test for long-term action of the compounds, the leaves were infected with an aqueous zoospore suspension of *Phytophthora infestans* one week after the application. The plants were subsequently kept in a chamber saturated with water vapor at 16–18° C. After 6 days, the tomato blight on the untreated but infected control plants had developed to such an extent that the infection could be determined visually in %.

In this test, the plants which had been treated with 16 ppm of the compounds I-1, I-2, I-5, I-6, I-7 and I-8 showed an infection of not more than 15%, while the plants which had been treated with 16 ppm of the comparative compounds A and B were infected to 25 and 100%, respectively, and the untreated plants were infected to 100%.

Use Example 3

Action Against *Puccinia Recondita* on Wheat (wheat leaf rust)

Leaves of potted wheat seedlings of the variety "Frühgold" were dusted with spores of the wheat leaf rust (*Puccinia recondita*). Thereafter, the pots were kept in a chamber of high atmospheric humidity (90 to 95%) and 20 to 22° C.for 24 hours. During this time, the spores germinated and the germ tubes penetrated into the leaf tissue. The next day, the infected plants were sprayed to runoff point with an aqueous active compound formulation which had been made up from a stock solution consisting of 10% of active compound, 63% of cyclohexanone and 27% of emulsifier. After spray coating had dried on, the test plants were cultivated in a greenhouse at 20–22° C. and 65–70% relative atmospheric humidity for 7 days. Thereafter, the extent of the rust fungus development on the leaves was determined.

In this test, the plants that had been treated with 16 ppm of the compounds I-1, I-2, I-3, I-6 and I-8 showed an infection of not more than 15% and the plants that had been treated with 63 ppm of the compounds I-1, I-2, I-3, I-6 and I-8 showed no infection, while the plants which had been treated with 16 and 63 ppm of the comparative compound A were infected to 75 and 40%, respectively, and untreated plants were infected to 75%.

Use Example 4

Action Against *Pyricularia Oryzae* (protective)

Leaves of potted rice seedlings of the variety "Tai-Nong 67" were sprayed to runoff point with an aqueous active compound formulation which had been made up from a stock solution of 10% of active compound, 63% of cyclohexanone and 27% of emulsifier. The next day, the plants were inoculated with an aqueous spore suspension of *Pyricularia oryzae*. The test plants were subsequently kept in conditioning chambers at 22–24° C. and 95–99% relative atmospheric humidity for 6 days. Thereafter, the extent of the development of the disease on the leaves was determined visually.

In this test, plants that had been treated with 63 ppm of compounds I-1, I-2, I-3, I-5 and I-8 showed an infection of not more than 15% and the plants that had been treated with 16 ppm of the compounds I-1, I-2, I-3, I-5 and I-8 showed an infection of not more than 40%, while the plants that had been treated with 63 and 16 ppm of the comparative compound A were infected to 60 and 90%, respectively, and untreated plants were also infected to 90%.

EXAMPLES OF ACTION AGAINST AMIMAL PESTS

The action of the compounds of the formula I against animal pests was demonstrated by the following experiments:

The active compounds were formulated a. as a 0.1% solution in acetone or b. as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil)

and diluted in the case of a. with acetone and in the case of b. with water to give the desired concentration.

After the experiments had ended, in each case the lowest concentration was determined at which the compounds still caused an 80 to 100% inhibition or mortality in comparison with untreated control experiments (critical or minimal concentration).

Example 1

Action Against *Nephotettix Cincticeps* (Green rice leafhopper), Contact Action

Filter paper dishes (Ø 9 cm) were treated with 1 ml of aqueous preparations of active compounds and subsequently populated with five adult leafhoppers. After 24 hours, the mortality was determined.

In this test, the active compound I-2 showed a critical concentration of 0.2 mg, while the comparative active compounds A and B had critical concentrations bf more than 0.2 mg.

We claim:

1. A substituted 2-(2'-pyridyloxy)phenylacetamide of the formula

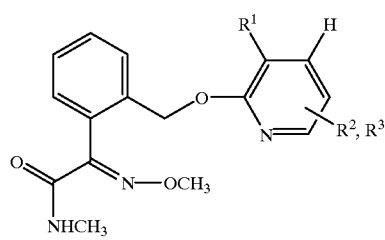

(I)

where
- R¹ is fluorine, chlorine, CH₃ or halomethyl;
- R² is fluorine, bromine, C₁–C₄-alkyl or halomethyl;
- R³ is hydrogen or one of the radicals mentioned under R²; or
- R² is 6-chloro if R³ is hydrogen,
- R³ is 5-chloro if R² is fluorine,
- and the compound in which R¹, R² and R³ are each chlorine;
- with the proviso that R¹ is not chlorine if R² is 5-trifluoromethyl and R³ is hydrogen.

2. A phenylacetamide of the formula Ia,

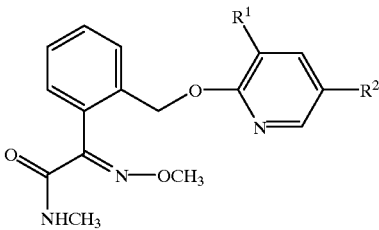

(Ia)

where R¹ and R² are each as defined in claim 1.

3. A phenylacetamide of the formula Ia as claimed in claim 2 where R¹ is methyl or trifluoromethyl.

4. A phenylacetamide of the formula Ia as claimed in claim 2 where one of the radicals R¹ or R² is methyl and the other is trifluoromethyl.

5. A phenylacetamide of the formula Ib,

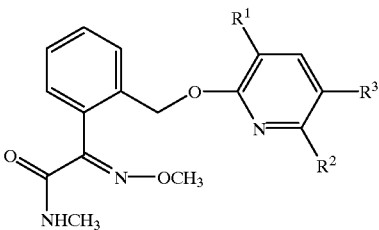

(Ib)

where R¹, R² and R³ are each as defined in claim 1.

6. A phenylacetamide of the formula Ib as claimed in claim 5 where R¹ is trifluoromethyl and R³ is hydrogen.

7. A process for preparing compounds of the formula Ia as claimed in claim 2, which comprises reacting a benzyl alcohol of the formula IIa

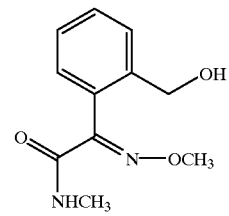

(IIa)

under basic conditions with a 2-halopyridine of the formula IIIa,

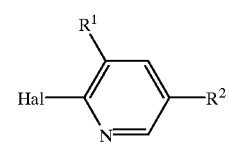

(IIIa)

in which Hal is halogen.

8. A process for preparing compounds of the formula Ib as claimed in claim 5, which comprises reacting a benzyl bromide of the formula IIb

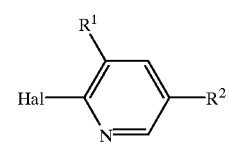

(IIb)

under basic conditions with a 2-hydroxypyridine of the formula IIIb

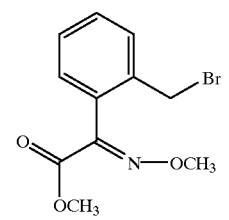

(IIIb)

to give a 2-(2'-pyridyloxy)phenylacetate of the formula IV

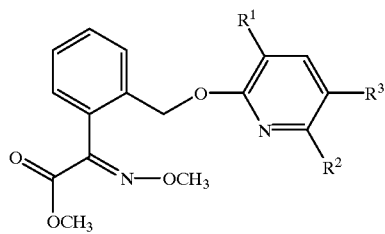

(IV)

and reacting IV with methylamine to give Ib.

9. A composition which is suitable for controlling animal pests or harmful fungi, comprising a solid or liquid carrier and an effective amount of at least one compound of the formula I as claimed in claim 1.

10. A method for controlling harmful fungi, which comprises treating the fungi, or the materials, plants, the soil or the seeds to be protected against fungal infection with an effective amount of at least one compound of the formula I as claimed in claim 1.

11. A method of controlling animal pests, which comprises treating the animal pests, or the materials, plants, the soil or the seeds to be protected against them with an effective amount of a compound of the formula I as claimed in claim 1.

* * * * *